(12) United States Patent
Victor

(10) Patent No.: US 10,376,180 B2
(45) Date of Patent: Aug. 13, 2019

(54) METHODS AND SYSTEMS FOR VERIFYING AND MONITORING ENDOTRACHEAL TUBE POSITION DURING INTUBATION

(71) Applicant: TELEFLEX MEDICAL INCORPORATED, Research Triangle Park, NC (US)

(72) Inventor: John C. Victor, Kunkletown, PA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 244 days.

(21) Appl. No.: 14/213,339

(22) Filed: Mar. 14, 2014

(65) Prior Publication Data

US 2014/0275958 A1 Sep. 18, 2014

Related U.S. Application Data

(60) Provisional application No. 61/784,043, filed on Mar. 14, 2013.

(51) Int. Cl.
*G01D 5/14* (2006.01)
*A61B 5/06* (2006.01)
(Continued)

(52) U.S. Cl.
CPC .............. *A61B 5/065* (2013.01); *A61M 16/04* (2013.01); *A61M 16/0411* (2014.02);
(Continued)

(58) Field of Classification Search
None
See application file for complete search history.

(56) References Cited

U.S. PATENT DOCUMENTS 5,425,382 A * 6/1995 Golden .................... A61B 5/06
128/899
2004/0011149 A1 * 1/2004 Carroll ................ G01D 5/3473
73/866.1

(Continued)

FOREIGN PATENT DOCUMENTS

JP 09-231889 A * 9/1997

OTHER PUBLICATIONS

"Review B: Coordinate Systems," Jan. 24, 2005, Department of Physics, Massachusetts Institute of Technology, pp. B-5 to B-8.*
(Continued)

*Primary Examiner* — Patricia J Park
(74) *Attorney, Agent, or Firm* — Baker & Hostetler LLP

(57) ABSTRACT

An endotracheal tube positioning device includes a first Hall sensor, a second Hall sensor spaced a predetermined distance from the first Hall sensor, a converter, and an integrated circuit board electrically connecting the first Hall sensor and the second Hall sensor to the converter, wherein a position range is established for the device based on a symmetry of voltage readings provided from the first and second Hall sensors to the converter. An endotracheal tube positioning system includes an endotracheal tube having a magnet provided toward a distal tip end, an endotracheal tube positioning device having a first Hall sensor and a second Hall sensor, the positioning device configured to adhere to a skin surface, and a monitor for receiving data based on voltage values provided by the first and second Hall sensors, the data indicating a position of the magnet relative to the adhered position of the positioning device.

11 Claims, 11 Drawing Sheets

(51) Int. Cl.
    *A61M 16/04*     (2006.01)
    *A61B 1/267*     (2006.01)

(52) U.S. Cl.
    CPC ........... *A61B 1/267* (2013.01); *A61B 2562/02* (2013.01); *A61M 2205/0272* (2013.01)

(56) References Cited

U.S. PATENT DOCUMENTS

| | | | |
|---|---|---|---|
| 2011/0031961 A1* | 2/2011 | Durand | A61B 1/267 324/207.2 |
| 2014/0058253 A1* | 2/2014 | Prough | A61B 5/0095 600/424 |

OTHER PUBLICATIONS

"Polynomial regression," Mar. 11, 2012, Wikipedia, "https://en.wikipedia.org/w/index.php?title=Polynomial_regression&oldid=481414105".*

* cited by examiner

Example:
Radius Polynomial / Power function for Z=20mm.
When "home is asserted by user and "Offset" is 0, "Angle" value is set to zero and Z value is determined by "Range". The appropriate Z Radius polynomial is then applied to H1V and H2V to calculate H1P and H2P.

METHODS AND SYSTEMS FOR VERIFYING AND MONITORING ENDOTRACHEAL TUBE POSITION DURING INTUBATION

CROSS-REFERENCE TO RELATED APPLICATIONS

This application claims priority to U.S. Provisional Patent Application No. 61/784,043, entitled, "METHODS AND SYSTEMS FOR VERIFYING AND MONITORING ENDOTRACHEAL TUBE POSITION DURING INTUBATION," filed Mar. 14, 2013, which is hereby incorporated by reference in its entirety.

FIELD OF THE INVENTION

The invention generally relates to endotracheal tube (ETT) placement, and, more particularly, to methods and systems for verifying and monitoring ETT position during intubation.

BACKGROUND OF THE INVENTION

Criticality of ETT placement during intubation has traditionally required the use of capnographic monitoring as well as radiograph imaging to avoid esophageal or bronchial installation. Either of these misplacement scenarios can result in inadequate patient ventilation and possible asphyxiation. In addition to the initial verification of the ETT device placement, subsequent verification radiographs are typically performed on a daily basis for patients requiring extended periods (e.g., days) of intubation.

A need exists for methods and systems that eliminate the expense and radiation exposure of repeated radiographs for intubated patients by providing a mechanism to verify ETT position through continuous monitoring and/or via an external reference or fiducial applied to the skin surface.

SUMMARY OF THE INVENTION

The foregoing needs are met by the present disclosure, wherein according to certain aspects, an endotracheal tube positioning device includes a first Hall sensor, a second Hall sensor spaced a predetermined distance from the first Hall sensor, a converter, and an integrated circuit board electrically connecting the first Hall sensor and the second Hall sensor to the converter, wherein a position range is established for the device based on a symmetry of voltage readings provided from the first and second Hall sensors to the converter.

In accordance with yet other aspects of the present disclosure, an endotracheal tube positioning system includes an endotracheal tube having a magnet provided toward a distal tip end, an endotracheal tube positioning device having a first Hall sensor and a second Hall sensor, the positioning device configured to adhere to a skin surface, and a monitor for receiving data based on voltage values provided by the first and second Hall sensors, the data indicating a position of the magnet relative to the adhered position of the positioning device.

In accordance with yet other aspects of the present disclosure, a method of positioning an endotracheal tube in a patient for intubation includes directing a distal tip end of the endotracheal tube through a glottis, the distal tip end having a magnet embedded therein, positioning the distal tip end at an home position in a mid-trachea region of the patient, affixing a sensing device just above or at a sternal notch of the patient, wherein the sensing device includes a first Hall sensor and a second Hall sensor positioned a predetermined distance from the first Hall sensor, reading with the sensing device an intensity of the magnetic field produced by the magnet using the first Hall sensor and the second Hall sensor, transmitting signals from the first Hall sensor and the second Hall sensor to a display device based on a voltage output sensitive to the intensity of the sensed magnetic field, determining a longitudinal displacement There has thus been outlined, rather broadly, certain aspects of the present invention in order that the detailed description herein may be better understood, and in order that the present contribution to the art may be better appreciated.

In this respect, before explaining at least one embodiment of the invention in detail, it is to be understood that the invention is not limited in its application to the details of the construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE DISCLOSURE

Figure 1:
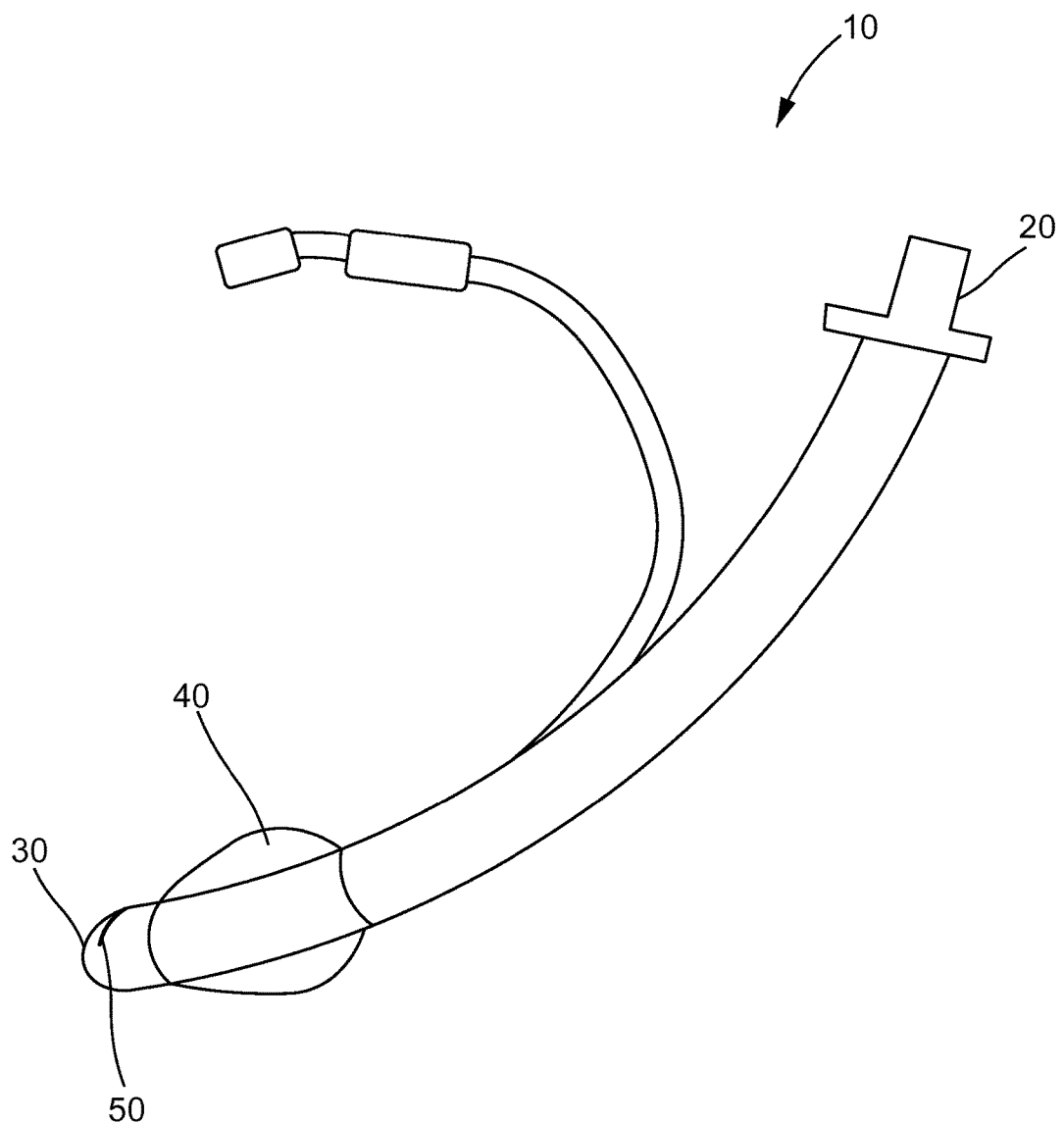
FIG. 1 illustrates an endotracheal tube, in accordance with aspects of the present disclosure.

The methods and systems disclosed herein enable precise tracking and control of the position of an ETT during intubation of a patient. As shown in FIG. 1, an ETT 10, which may be made from polyvinyl chloride (PVC) or any other suitable material, has a proximal end 20 and a distal tip end 30. The ETT may be used to establish a patient airway during a medical procedure by inserting the distal tip end 30 of the ETT into the trachea, typically through the mouth, which procedure is known as intubation. Once inserted to a correct position in the trachea, a cuff balloon 40 may be inflated in an attempt to lock the ETT at the correct position. Once established, the ETT may be used to deliver gases, such as oxygen, helium, nitrous oxide, to name a few, drugs, including those used for general anesthesia and medicines, and/or to provide a pathway for mechanical ventilation to a patient when the proximal end 20 of the ETT is coupled to a mechanical ventilator, for example.

Placement of the ETT is critical during intubation to avoid esophageal or bronchial installation. Either of these misplacement scenarios can result in inadequate patient ventilation and possible asphyxiation. Today's standard of care involves intubating the patient with the ETT so that the distal tip end 30 is directed through the glottis and positioned in the mid-trachea approximately 2 cm above the bifurcation of the carina. Capnography may be used to verify initial placement. In addition, the patient is often given a chest x-ray to confirm the proper placement of the ETT by visualizing the placement of the distal end tip 30 with respect to the carina.

Due to many factors, including each patient's individual physiology, a patient's voluntary or involuntary attempts to extubate the ETT, and the fact that patients are subjected to movement during a procedure and/or transport, there is ample opportunity for the distal end tip 30 of the ETT to move from the initially confirmed position. Accordingly, particularly during extended intubation of a patient over multiple days, each intubated patient is often subjected to at least one and often multiple confirmatory x-rays every day the patient is intubated to ensure proper positioning of the ETT.

Aspects of the present disclosure provide methods and systems for monitoring the proper placement of the ETT by transcutaneous determination of the position of the distal end tip 30 of the ETT. As shown in FIG. 1, a miniature rare earth magnet 50 may be embedded in a lumen wall of the ETT 10 near the distal end tip 30. The magnet 50 may be radially polarized to provide the greatest B-field flux density in a plane orthogonal to a circumferential surface (not edge) of the magnet 50.

Figure 2:
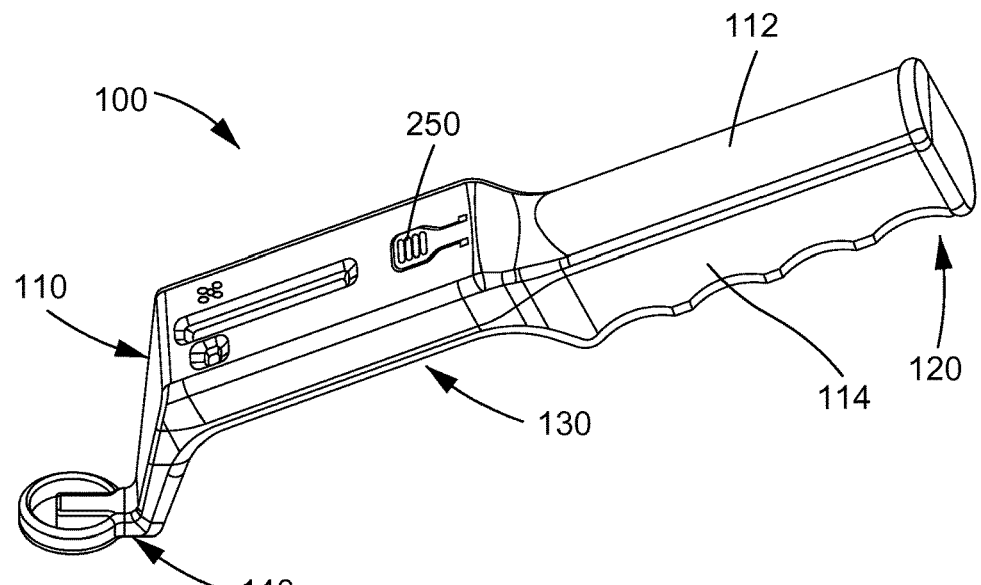
FIG. 2 illustrates a monitoring device, in accordance with aspects of the present disclosure.
Figure 3:
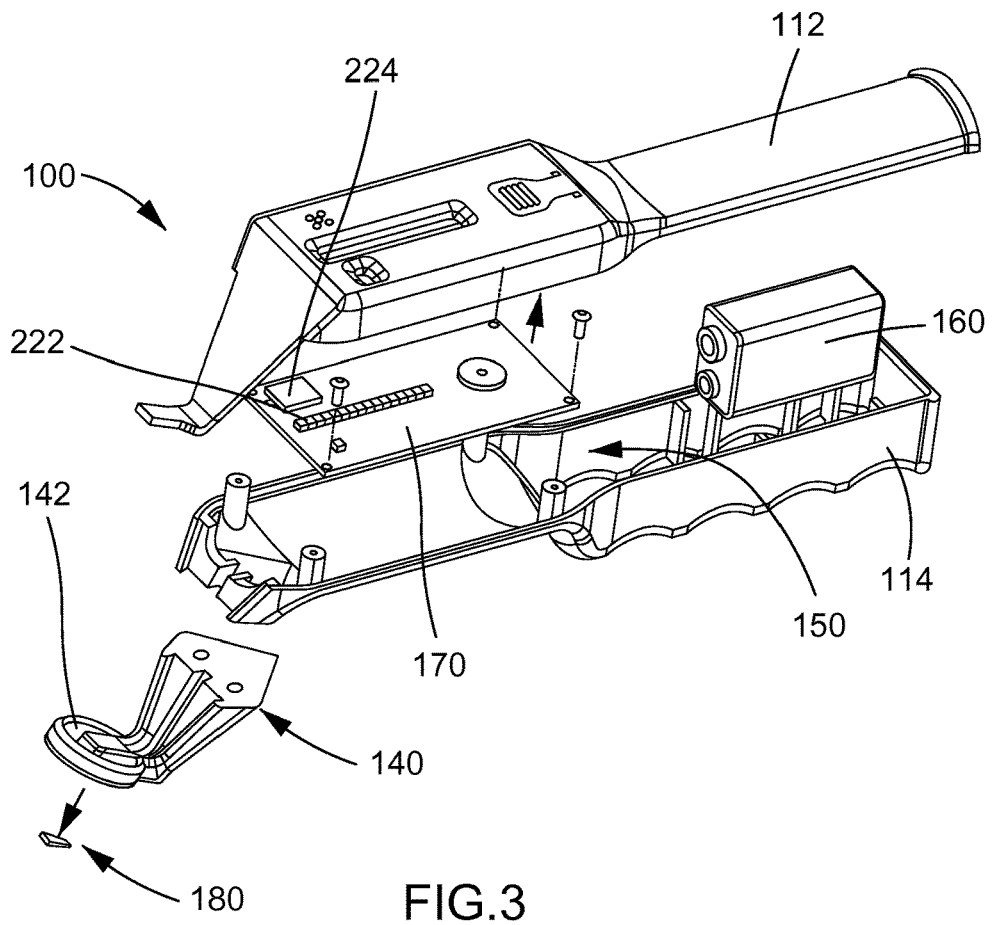
FIG. 3 shows an exploded view of a monitoring device, in accordance with aspects of the present disclosure.

As illustrated in FIGS. 2 and 3, a small battery powered hand held device 100 may be used to transcutaneously measure the intensity of the B-field. The device 100 may include a housing 110 having an upper housing portion 112 and a lower housing portion 114 coupled together to form a handle portion 120 at a proximal end, a central body portion 130, and a sensing tip portion 140 extending from a distal end of the body portion 130. The upper housing portion 112 and lower housing portion 114 may be coupled, for example, by press or snap fit and/or by any suitable attachment means, including screws, tabs, and adhesives, to form a hollow interior chamber 150 for mounting and protecting a power source 160, such as a battery, and electrical circuitry, some of which may be implemented via an Integrated Circuit Board (ICB) 170. The sensing tip portion 140 of the housing may be an integrally formed feature of the housing 110 and/or all or a portion of the sensing tip portion 130 may be separately formed, as shown in FIG. 3, and attached to the housing 110.

Figure 4:
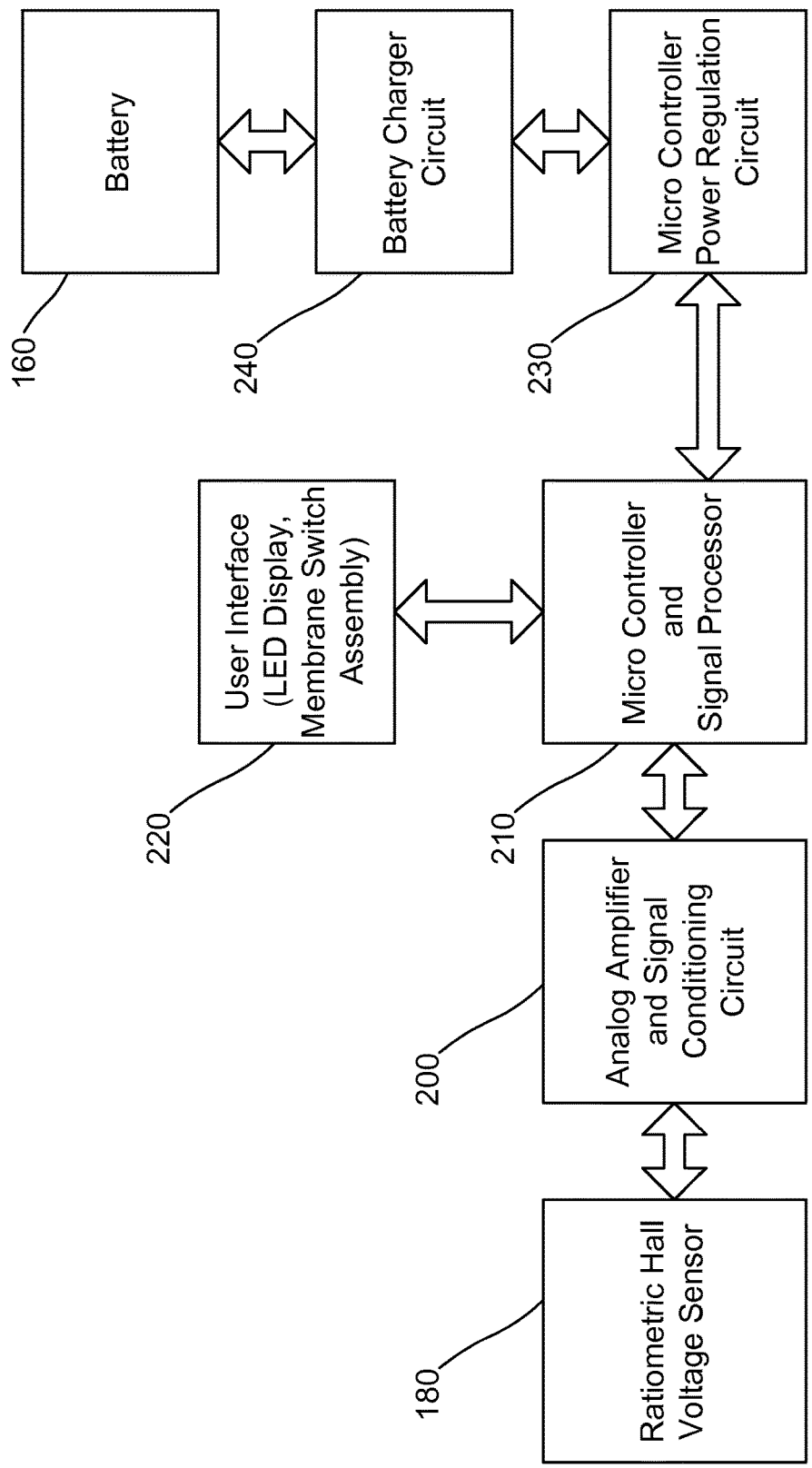
FIG. 4 is a block diagram illustrating components of a monitoring device, in accordance with aspects of the present disclosure.

As shown in FIG. 3, a ratiometric Hall sensor 180 may be mounted and retained in a tip end 142 of the sensing tip portion 140 of the device 100. FIG. 4 illustrates aspects of the electrical circuitry of the device 100, which may include various means for electrically connecting to the sensor 180 an analog amplifier and signal conditioning circuit 200, a micro controller and signal processor 210, a user interface 220, a micro controller power regulation circuit 230, a battery charger circuit 240, and/or the power source 160, which may be a battery, for example. An output of the sensor 180 measures the Hall voltage, which may be conditioned, amplified, and passed to a 12 bit analog to digital conversion stage via the analog amplifier and signal conditioning circuit 200. The digital Hall voltage value may then be interpreted by an algorithm executing within the micro controller and signal processor 210. The device 100 may permit the user to null the B-field signal in order to eliminate the influence of any spurious environmental B-fields.

As the device sensor 180 approaches a B-field source, the device 100 may provide both visual and audio indication of absolute field intensity via the user interface 220. For example, a visual indicator 222 may consist of a 16 element bar graph of Light Emitting Diodes (LEDs), as shown in FIG. 3, and an audio indication may provide the user with a constant pitch, frequency varying tick via an audio device 224. The visual indicator 222 may employ a peak hold mechanism, wherein if a B-field source is approached and then passed, the peak value LED will remain illuminated although the graph elements inferior to the peak LED will continue to respond dynamically to the B-field value. The illumination of peak value LED will be maintained until the user initiates a null process, which may be by pressing a control button 250 (see FIG. 2). The control button 250 may also provide on/off control of the device, which may be by pressing the button 250 for an extended time compared to, for example, activation of the null process which may be accomplished by a one-time pressing of the button 250.

Following radiograph or x-ray verification of correct ETT positioning, the Hall sensing device 100 may be swept over the patient's throat, preferably by approaching the patient's sternal notch from above or below. The visual and audio indicators, 222 and 224, will provide a peak value hold condition when the sensor tip sensor 180 is located directly above the magnet 50, indicating the ETT tip position. A fiducial, such as an adhesive patch or ink, may then be applied on the patient's skin corresponding to the location of the tip end 142 of the device 100. The Hall effect ETT position can now be re-verified at any time by positioning the tip end 142 of the Hall sensor device 100 over the fiducial or re-sweeping the Hall sensor device 100 to establish the extent of ETT displacement from the original verified position. If displaced, a clinician could reposition the ETT by further intubating and/or extubating, i.e., pushing in or pulling back, the ETT according to the noted distance of displacement. The process may be repeated until the clinician has verified the ETT is once again at the proper placement position as initially determined for maximum safety and effectiveness.

Configuration testing indicates reproducible position detection accuracy of +/−5 mm through 40 mm of tissue analog. These accuracy estimates are well within the nominal distance from larynx to carina for normal positioning of the ETT for effective ventilation.

Figure 5:
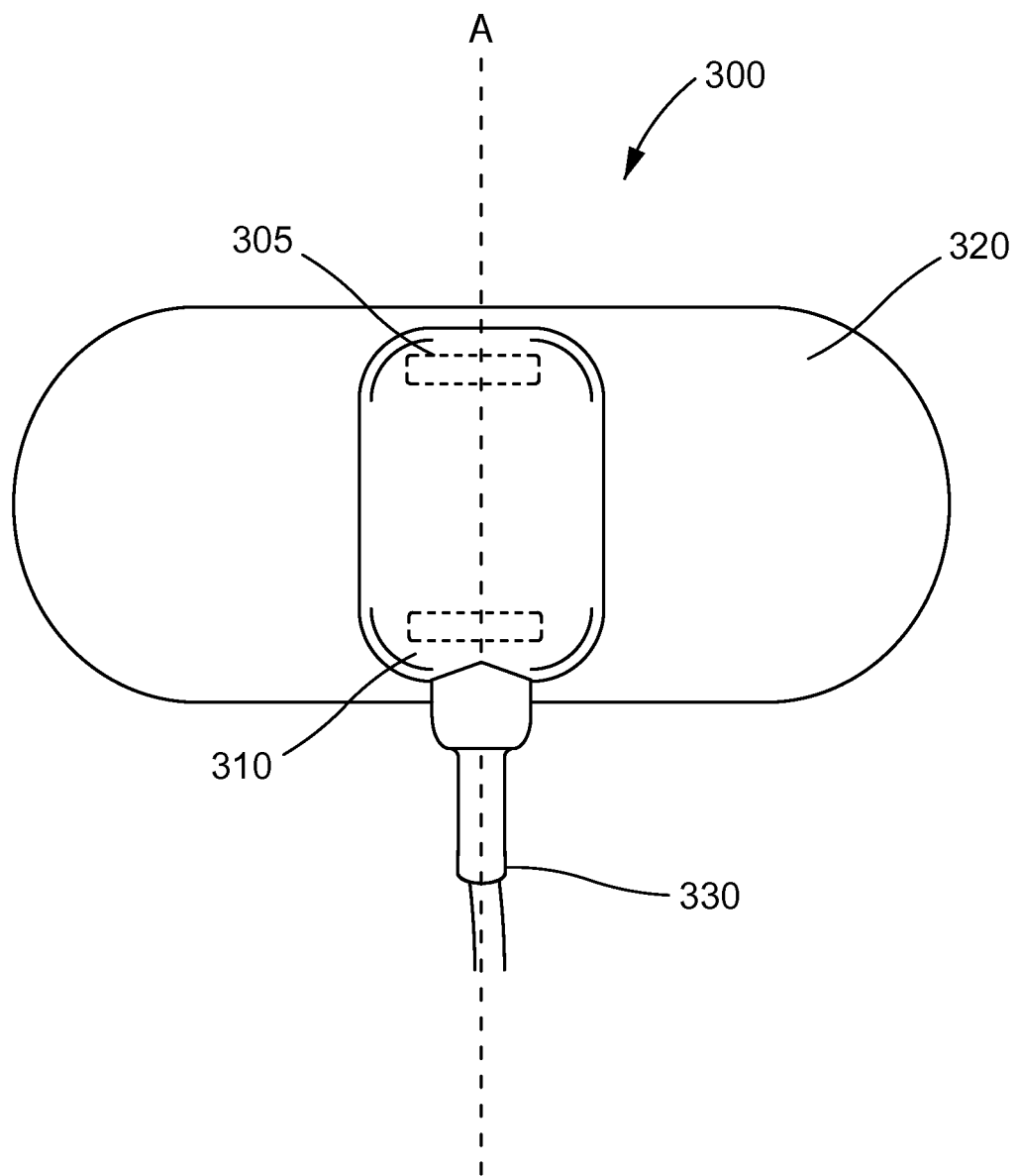
FIG. 5 illustrates a positioning device, in accordance with aspects of the present disclosure.

In accordance with yet other aspects of the present invention, FIG. 5 illustrates a dual sensor device 300 useful for continuous monitoring of the ETT position in a patient. The dual sensor device 300 may be formed to house a first Hall sensor 305 and a second Hall sensor 310. Two sensors allow a refined determination of the distance of migration of the ETT 10 from an ideal initially determined position as well as the direction of migration of the ETT 10 from the ideal initially determined position. Because the dual sensor device 300 may be affixed to the patient for continuous monitoring, the sensor device 300 allows for autonomous repositioning of the ETT without having to hold or sweep the sensor device 300 to obtain a Hall voltage reading for position determination.

As shown in FIG. 5, the two Hall voltage sensors 305 and 310 may be mounted in the sensor device 300 at a set distance apart, preferably about 1 cm apart along a longitudinal centerline A of the device 300. A small ICB 315 (see FIG. 8) may be used to mount the sensors 305 and 310 and associated electrical circuits.

Figure 6:
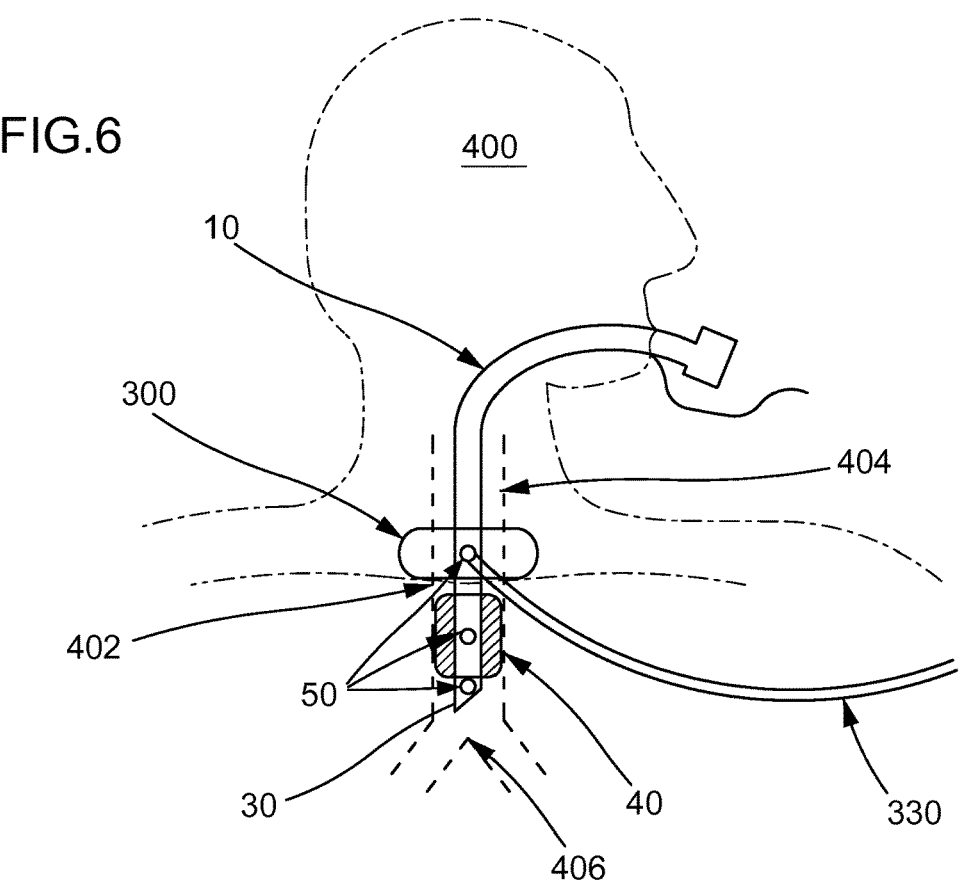
FIG. 6 illustrates an endotracheal tube and a positioning device in a state of use, in accordance with aspects of the present disclosure.
Figure 7:
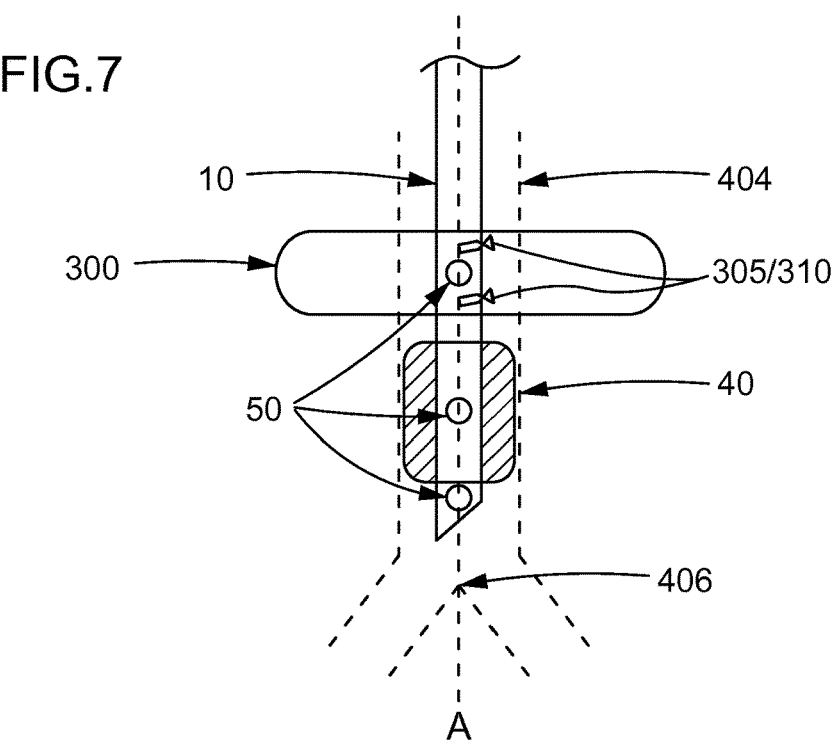
FIG. 7 is a close up frontal view of an endotracheal tube and a positioning device in a state of use, in accordance with aspects of the present disclosure.

As shown in FIGS. 6 and 7, the device 300 may be affixed to a patient 400 just above or at the sternal notch 402. The ETT 10 may be inserted so that the distal tip end 30 is directed through the glottis and positioned in the mid-trachea 404 approximately 2 cm above the bifurcation of the carina 406. The cuff 40 may be inflated to establish and secure the ETT in position. Capnography may be used to verify initial placement. In addition, the patient may be given a chest x-ray to confirm the proper placement of the ETT 10 by visualizing the placement of the distal end tip 30 with respect to the carina 406.

Figure 8:
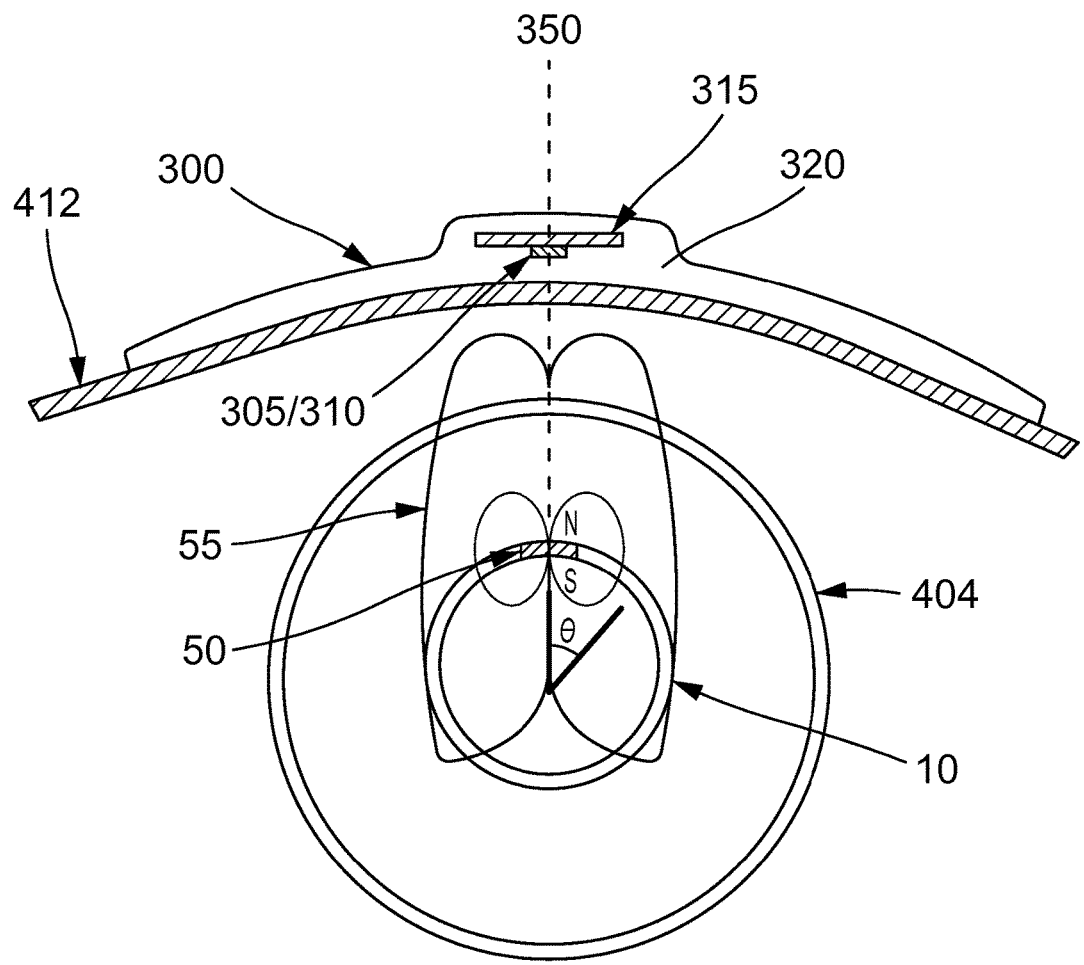
FIG. 8 illustrates a top view of an endotracheal tube and a positioning device in a state of use, in accordance with aspects of the present disclosure.

As shown in FIG. 8, the device 300 may be composed of a skin barrier layer, for example, over-molded with silicone, so that the device may be easily affixed in position against the skin surface 412. The ICB 315 and sensors 305/310 may be mounted into a housing structure or the silicone may be over-molded over the ICB 315 and sensors to form a body 320. The device 300 may be shaped similar to a bandaid, for example, for efficient visual directional coordination when affixing the sensor device 300 to a patient.

Figure 9:
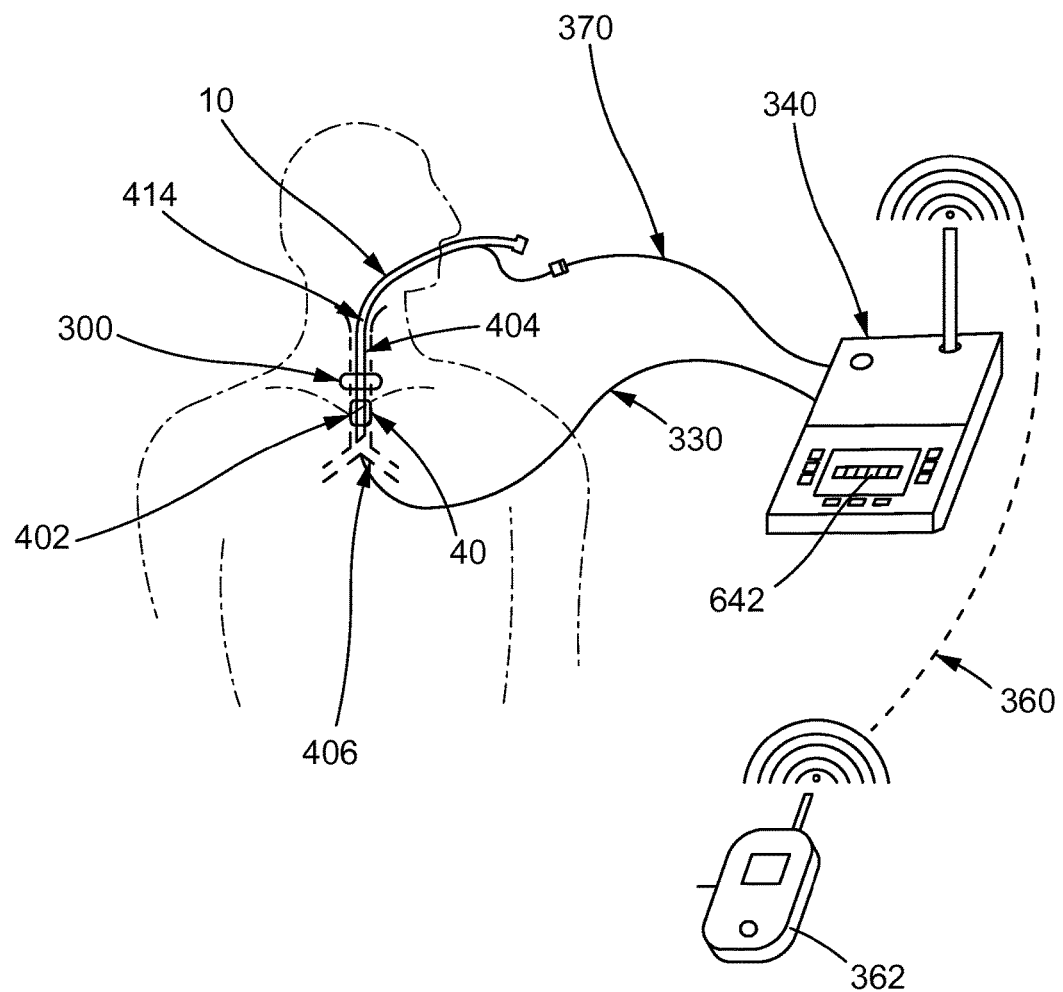
FIG. 9 illustrates an ETT tube monitoring system, in accordance with aspects of the present disclosure.

As shown in FIG. 9, signals from the sensors 305 and 310 in the positioning device 300 may be electrically conducted via four conductors, typically a 5V conductor and a ground connection for each of the sensors, via a tether 330 connected to a monitoring apparatus 340. With the ETT 10 inserted through the larynx 414 and positioned in the trachea 404, the Hall sensors 305 and 310 in the positioning device 300 produce a voltage output sensitive to the intensity of the magnetic field produced by the magnet 50. The sensors 305 and 310 may have a sensitivity of 5 mv/gauss, for example.

Referring back to FIG. 8, by using a cylindrical coordinate system, wherein the ETT 10 is defined as being a substantially cylindrical unit, any point on the ETT 10 may be defined according to a longitudinal coordinate along the length of the ETT 10 and a corresponding radial coordinate along the circumference of the ETT 10. Accordingly, once an initial position of the ETT is determined, the sensor device 300 may be used to determine longitudinal displacement of the ETT 10 as well as an angle of rotation θ of the ETT 10 from a polar axis 350 established when the magnet 50 is anteriorly aligned with the sensors 305/310.

The magnetic field 55 of the magnet 50 may be defined according to the choice of magnet material over a region and cylindrical radius to accommodate substantially any patient anatomy. A series of curves may be derived to represent the magnetic field as the sensor moves in the longitudinal axis and as a function of radial rotation. Rather than use large look up tables corresponding to predetermined experimental values of magnetic field strength for every possible longitudinal and radial point with respect to the sensor positions, higher order polynomial equations may be derived to fit to the predetermined curves so the magnetic field strength with respect to each sensor may be determined at any given longitudinal and radial point with respect to a central axis of an ETT of given radius. Thus, for every point in the cylindrical coordinate system, two unique sensor values may be determined. By mapping the baseline coordinate system to the initial confirmed position for an ETT of radius Z, the predetermined polynomials may be used to determine subsequent changes in position based on new sensor values, which may be continuously monitored.

Figure 10:
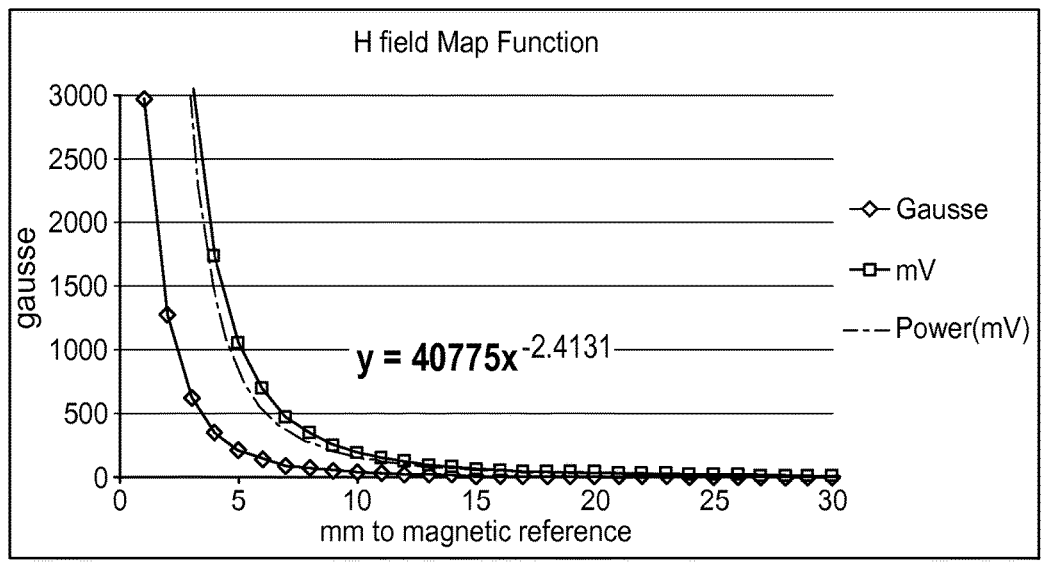
FIG. 10 illustrates an example of a predetermined radius polynomial series, in accordance with aspects of the present disclosure.

For example, as shown in FIG. 10, for an ETT 10 having a radius Z of 20 mm, a predetermined radius polynomial series may be used to determine the longitudinal position relative to an ETT home reference, also taking into account an angle correction coefficient. The recorded Hall voltage H1V of the first sensor 305 and the Hall voltage H2V of the second sensor 310 may be used in the radius polynomial, for example, to determine the longitudinal position of the ETT 10 in the trachea based on calculated relative longitudinal positions H1P and H2P.

Figure 11:
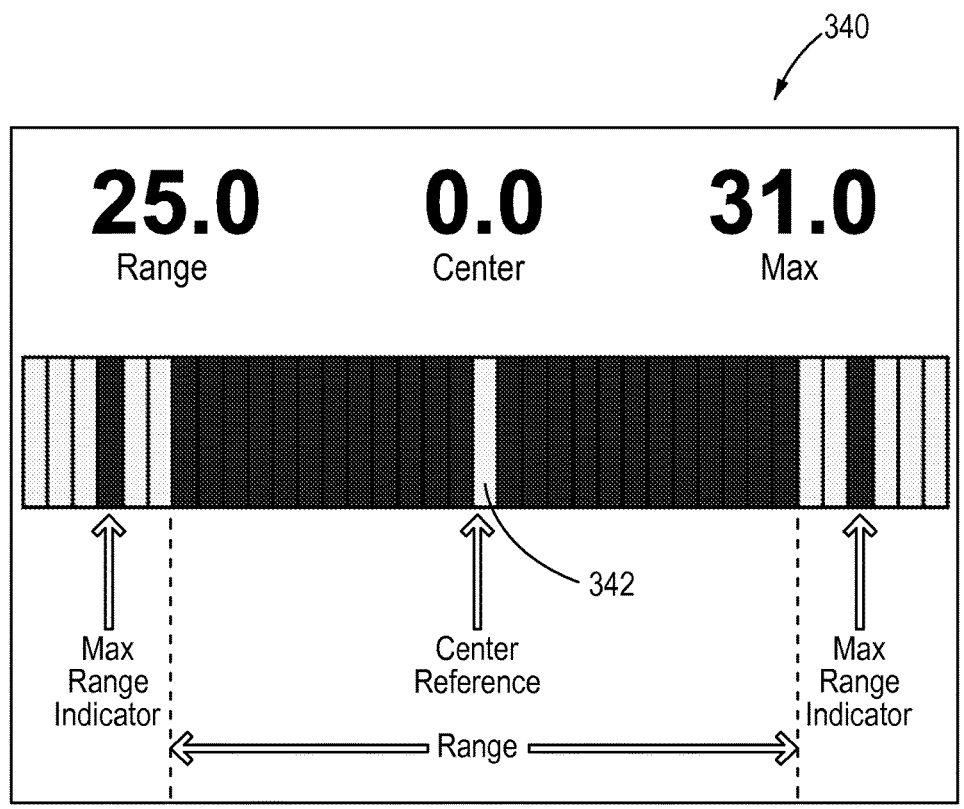
FIG. 11 shows an exemplary display illustrating aspects of monitoring placement of an ETT using a positioning device, in accordance with aspects of the present disclosure.
Figure 12:
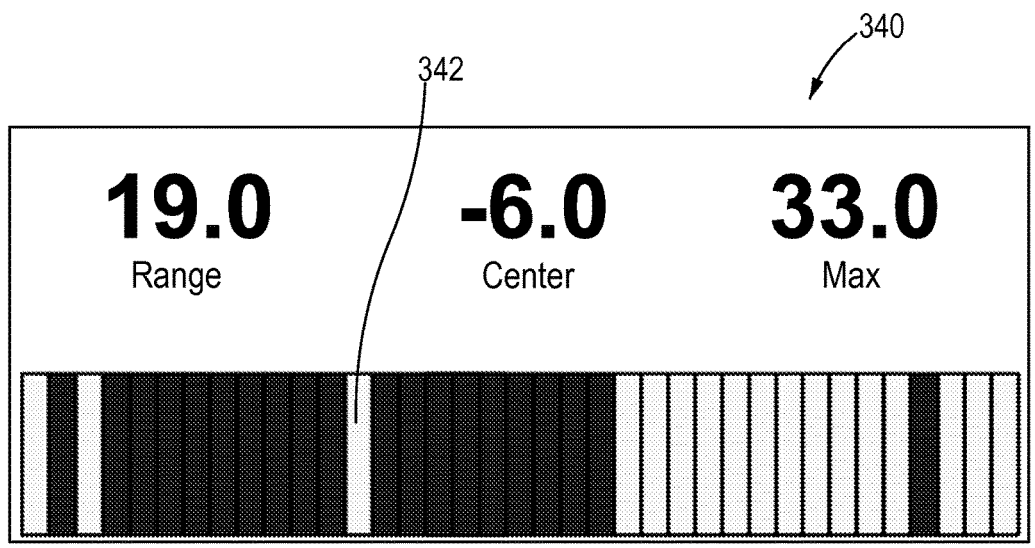
FIG. 12 shows another view of an exemplary display illustrating aspects of monitoring placement of an ETT using a positioning device, in accordance with aspects of the present disclosure.

As shown in FIGS. 7 and 8, with the ETT 10 in the initial confirmed proper position, the sensor 300 may be located near the sternal notch on a patient. Because the magnet 50 is in a known radial position in the trachea, preferably nearest the anterior portion of the throat, longitudinal movement of the sensor 300 up or down along the centerline A (see FIG. A), substantially parallel to a central axis of the trachea, will allow the clinician to set the center point position of the sensor 300, which may be referred to as the "Home" position. As shown in FIGS. 11 and 12, the two Hall voltage signals may be processed and displayed on the monitoring apparatus 340, such as a portable electronic device or a computer monitor, for example, in a way that is easy for the clinician to decipher. FIG. 11 illustrates the Home position in which a center reference line 342 on the display indicates that the magnet is longitudinally centered between the two Hall sensors 305, 310. In FIG. 12, the monitoring apparatus 340 shows, for example, that the centerline 342 has shifted, indicating that the ETT 10 has moved and/or rotated such that the magnet 50 is closer to one of two sensors 305, 310 and further from the other one of the two sensors 305, 310. In accordance with certain aspects of the present disclosure, an audio and/or visual alarm may be activated if the device 300 detects movement of the magnet 50 beyond a certain predetermined range. In accordance with yet other aspects of the present disclosure, as shown in FIG. 9, the signals received and processed by the monitoring apparatus 340 may be sent, for example, via an interface 360, such as a radio frequency interface, to a remote receiver 362. Thus, a technician may monitor or be alerted by alarm, for example, to the position of the ETT in any given patient, or even a plurality of patients, without having to be physically present. The continuous and/or remote monitoring capabilities of the positioning device 300 provide a safe, effective method of tracking ETT position without the need to manually observe or periodically assess the position with x-ray, for example.

Figure 13:
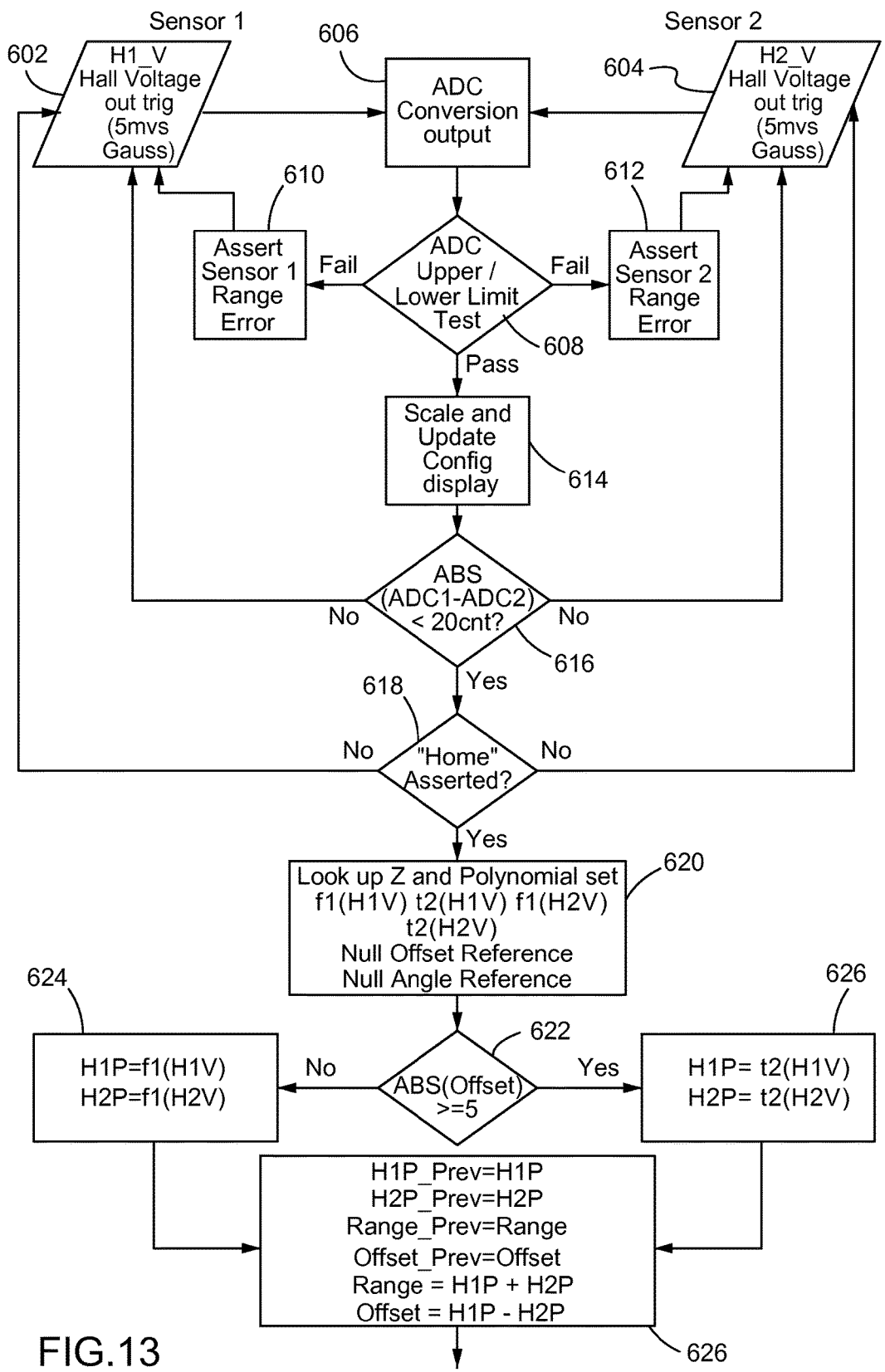
FIGS. 13 and 14 illustrate a method for monitoring placement of an ETT using a positioning device, in accordance with aspects of the present disclosure.
Figure 14:
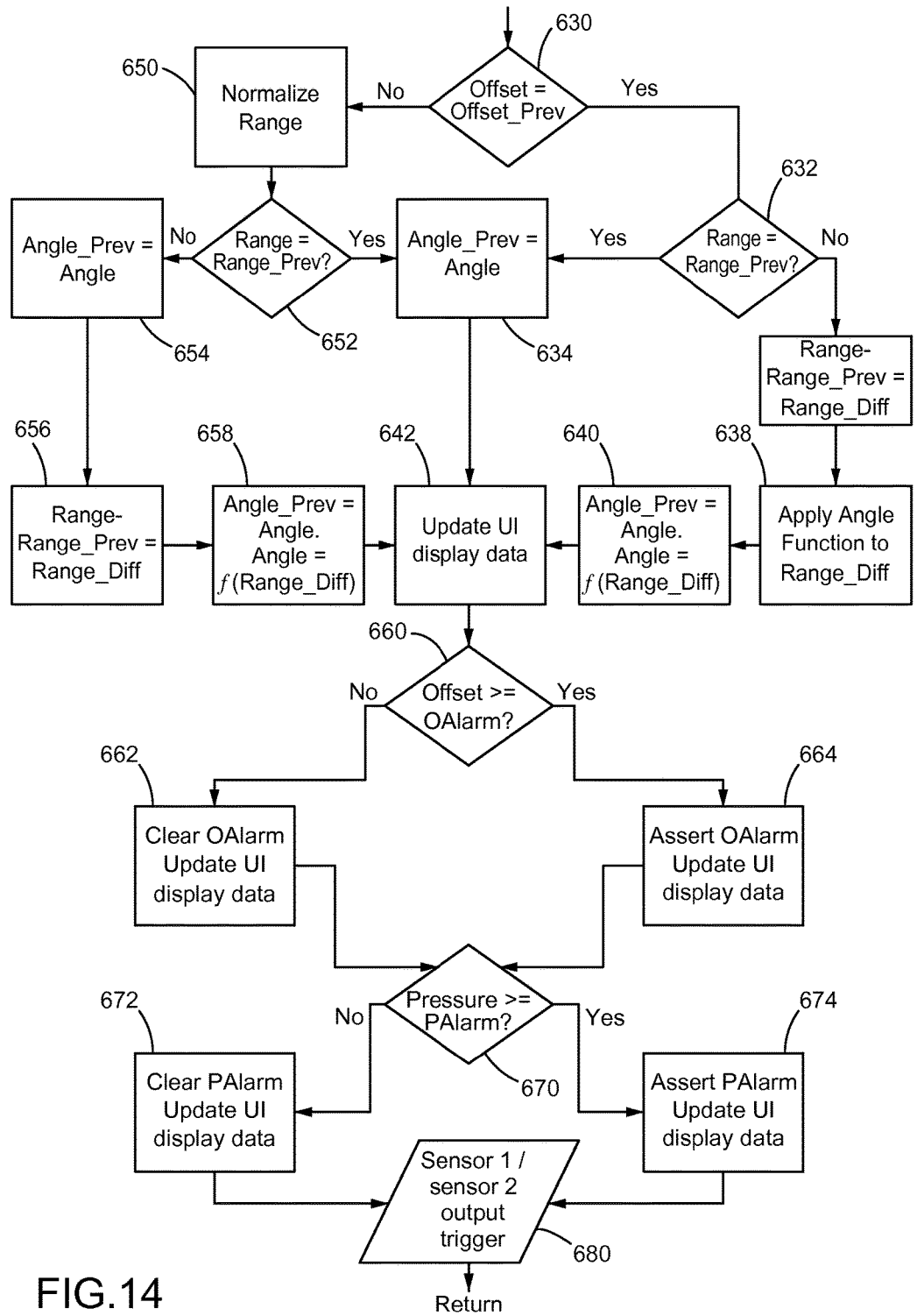

FIGS. 13 and 14 illustrating a method of monitoring ETT positioning using the positioning device 300 and an ETT with an embedded magnet 50. Beginning with FIG. 13, the positioning device 300 must first be calibrated. With the ETT verified to be in a desired position, the positioning device 300 may first be placed near the sternal notch of the patient. A sweeping of the device 300 up and down longitudinally allows the Hall sensors 305 and 310 to begin reading the intensity of the magnetic field of the magnet 50 embedded at a particular longitudinal position of the ETT. As shown at 602 and 604, each of the Hall sensors in the device 300 generate a respective voltage according to the intensity of the magnetic field that is output to an analog/digital converter 606. The converter 606 reads the output from the sensors, including a maximum upper limit range indicator reading (see FIG. 11) corresponding to, for example, a maximum longitudinal distance in one direction where a signal from one of the sensors 305 or 310 becomes negligible. A maximum lower limit range indicator reading may similarly be produced corresponding to an opposite maximum range produced when a reading from the other of the sensors 305 or 310 becomes negligible. Anywhere beyond the maximum upper limit or maximum lower limit and the voltage readings of one and/or both of the sensors indicate the device 300 is not in proper position for adequate fine tuning positional adjustment in order to affix the device 300 at a "home" position for continuous monitoring. Thus, as shown in FIG. 13, if either of the upper or lower range limits are reached as read by the converter at step 608, a range error may be generated at 610 or 612 depending on which sensor 305 or 310 is essentially beyond range for obtaining an adequate voltage reading. Additional readings are read by the converter 606 until the reading indicates that both sensors 305 and 310 are providing readings to the converter 606 within the acceptable limits.

An adequate range reading is established based on symmetry of the sensors 305 and 310 in relation to the magnet 50. When centered in the home position, as shown in FIG. 11, each sensor reads an approximately equal value with respect to the intensity of the magnetic field and a centerline may be used to indicate on a display to the user that the device 300 is properly centered and in position. As the device 300 is moved up or down, one sensor will read an increasing intensity and the other sensor will read a decreasing intensity of the magnetic field. Referring back to FIG. 13, once the device 300 passes the upper and lower limit test at 608, the scaled display may be updated at step 614. The centerline 342 shown in FIGS. 11 and 12 may be updated to reflect movement of the range based on each of the voltage readings 602 and 604 received by the converter 606. At step 616, the readings and configuration of the display are continuously updated until the voltage readings of each sensor are approximately equal, at which point the user may indicate that the device 300 is in the proper home position at step 618. Once the home position is established, at step 620 the radius polynomial for an ETT of given radial dimension is applied to the Hall voltage readings established for the home position, setting a home longitudinal reference value for each of the sensors, H1P and H2P, and a home angle reference value which is the sensor axis rotational position relative to the ETT home reference. The longitudinal range may be established by adding the H1P value to the H2P value.

At step 622, for each successive sensor reading, an offset is determined to see if the ETT has moved relative to the static home position of the positioning device 300. If the values of H1P and H2P are equal, wherein the sensors are symmetrically aligned around the magnet, as is the case when the device 300 is in the home position, then an offset, which is H1P-H2P, is zero, indicative that the ETT has not moved. As shown at step 624, the H1P and H2P values remain the same, as does the range value, for example. However, if successive readings taken at step 620 establish at step 622 that there is an offset, the new values of H1P and H2P are determined at step 626 and recorded at step 628. As shown in FIG. 14, it is determined at step 630 whether the offset recorded at step 628 is the same as the previous offset reading or if the ETT has experienced additional displacement. If the offset value is the same as the previous reading, a range reading is taken at step 632. If the range reading is the same as the previous range reading, the angle has not changed and the angle is set at step 634 to be the same as that of the previous offset. If, however, the range is different at step 632, the range difference is noted at step 636. At step 638, an angle function is applied based on the range difference to determine at step 640 a new angle of rotation. In this case, the range difference occurs when the longitudinal offset has not changed but the voltage readings of the sensors 305 and 310 indicate a rotational change in the position of the magnet 50. The new angle is submitted to update the user interface at step 642.

Referring back to step 630, if it is determined that the offset of the current reading is different from the offset of the previous reading, a range normalization is performed at step 650 and the normalized range is compared to the previous range reading at step 652. If the range readings are equal, indicating that the angle of rotation has not changed, the angle determination at step 634 is the same as that of the previous angle. In this case, the new offset is indicative of a longitudinal movement of the device 300, which is provided to the user interface display at step 642. If, however, at step 652, the range reading differs from the previous range reading, the previous angle is noted at step 654 and a range difference determined at step 656 is used to determine a new angle at step 658. The new angle may be provided to the user interface display at 642.

In step 660, the offset value is compared to a threshold offset value to determine if an alarm or alert must be sent to notify a technician that the ETT has moved. The user interface display data at 642 may be updated as shown at 662 and 664 depending on whether an alarm situation is indicated. The technician may reposition the ETT based on the system feedback until the offset is nullified.

In accordance with yet other aspects of the present invention, as shown in FIG. 9, for example, a cuff pressure monitor 370 may be used to provide cuff pressure data to the user interface display 642. In this manner, as shown in FIG. 14, step 670 may include determining whether the cuff pressure is above or below a threshold value such that an alarm or alert must be sent to notify a technician. The user interface display data at 642 may be updated as shown at 672 and 674 depending on whether an alarm situation is indicated. At step 680, a sensor output is triggered and the entire process is repeated beginning with the voltage readings at 602 and 604 being provided to the converter 606.

It is to be understood that any feature described in relation to any one aspect may be used alone, or in combination with other features described, and may also be used in combination with one or more features of any other of the disclosed aspects, or any combination of any other of the disclosed aspects.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

What is claimed is:

1. A method of positioning an endotracheal tube in a patient for intubation, the method comprising:
    providing a sensing device;
    directing a distal tip end of the endotracheal tube through a glottis, the distal tip end having a magnet embedded in a lumen wall of the endotracheal tube;
    positioning the distal tip end at a home position in a mid-trachea region of the patient;
    affixing the sensing device just above or at a sternal notch of the patient, wherein the sensing device includes a first Hall sensor and a second Hall sensor positioned at a predetermined distance from the first Hall sensor;
    reading with the sensing device an intensity of a magnetic field produced by the magnet using the first Hall sensor and the second Hall sensor;
    receiving, with a display device in communication with one or more processors, signals from the first Hall sensor and the second Hall sensor in the sensing device corresponding to a voltage output that is sensitive to an intensity of the magnetic field;
    defining, with the one or more processors, any point on the endotracheal tube according to a longitudinal coordinate along a length of the endotracheal tube and a corresponding radial coordinate along a circumference of the endotracheal tube using a cylindrical coordinate system;
    establishing a home position of the sensing device and applying a radius polynomial for the endotracheal tube to the Hall sensor readings established for the home position of the sensing device, setting a home longitudinal reference value for each of the Hall sensors and a home angle reference value indicative of a relative rotation of the endotracheal tube with respect to each of the Hall sensors;
    determining, with the one or more processors, a longitudinal displacement of the endotracheal tube relative to the home position of the sensing device based on signals of successive sensor readings of the first and second Hall sensors;
    determining, with the one or more processors, a radial displacement of the endotracheal tube relative to the home position based on the signals of the successive sensor readings of the first and second Hall sensors when the magnet is anteriorly aligned with both the first and second Hall sensors, and
    displaying, with the display device, a display corresponding to at least one of the longitudinal displacement and the radial displacement.

2. The method of positioning an endotracheal tube of claim 1, wherein the home position is approximately 2 centimeters above a bifurcation of a carina of the patient.

3. The method of positioning an endotracheal tube of claim 1, further comprising:
    verifying the home position of the distal tip end with respect to the carina via a visualization means.

4. The method of positioning an endotracheal tube of claim 1, further comprising:
    sending an audio and/or visual alarm when the sensing device detects the longitudinal or radial displacement of the endotracheal tube beyond a predetermined range.

5. The method of positioning an endotracheal tube of claim 1,
    wherein the sensing device is affixed at a position corresponding to the home position of the endotracheal tube based on Hall voltage readings produced by the first Hall sensor and the second Hall sensor indicating each Hall sensor is reading an equal intensity of the magnetic field.

6. The method of positioning an endotracheal tube of claim 1, further comprising:
    connecting the display device to the sensing device for receiving data based on voltage values provided by the first Hall sensor and the second Hall sensor,
    wherein the display device is a monitor and the data indicates a position of the magnet relative to the affixed position of the sensing device.

7. The method of positioning an endotracheal tube of claim 1, wherein the magnet is longitudinally centered between the first and second Hall sensors when the distal tip end of the endotracheal tube is at the home position.

8. The method of positioning an endotracheal tube of claim 1, wherein establishing the home position of the sensing device is based on the signals from the first and second Hall sensors, the home position of the sensing device indicating each respective signal from the first and second Hall Sensors is approximately equal.

9. A method of positioning an endotracheal tube having a radial dimension in a patient for intubation, the method comprising:
    positioning a distal tip end of the endotracheal tube in a mid-trachea region of the patient, the distal tip end of the endotracheal tube having a magnet embedded therein;
    providing a sensor device including a first Hall sensor and a second Hall sensor, the first and second Hall sensors spaced apart by a predetermined distance;
    placing the sensor device just above or at a sternal notch of the patient;
    sensing, with the first Hall sensor and the second Hall sensor, a magnetic field produced by the magnet embedded in the endotracheal tube when the magnet is anteriorly aligned with both the first and second Hall sensors;
    determining a home position of the sensor device based on Hall voltage readings produced by the first and second Hall sensors indicating each Hall sensor is reading an approximately equal intensity of the magnetic field, and setting a home longitudinal reference value for each Hall sensor and a home angle reference value indicative of a relative rotation of the endotracheal tube with respect to each of the Hall sensors;
    receiving data for successive sensor readings based on voltage values provided by the first and second Hall sensors, the data indicating a position of the magnet of the endotracheal tube relative to the position of the sensor device;
    determining, from the data, a longitudinal offset value based on a longitudinal displacement determined when one of the first or second Hall sensors reads an increasing intensity of the magnetic field and the other one of the first or second Hall sensors reads a decreasing intensity of the magnetic field;
    determining, from the data, a rotational change in the position of the magnet; and displaying on a monitoring apparatus at least one of the longitudinal displacement of the endotracheal tube relative to the sensor device and the rotational change of the endotracheal tube relative to the sensor device.

10. The method of positioning an endotracheal tube of claim 9, further comprising activating an audio and/or visual alarm if the sensor device detects movement of the endotracheal tube beyond a predetermined range.

11. The method of positioning an endotracheal tube of claim 10, wherein the predetermined range includes a longitudinal component and a radial component.

\* \* \* \* \*